US00PP12947P2

(12) United States Plant Patent
Rother

(10) Patent No.: US PP12,947 P2
(45) Date of Patent: Sep. 10, 2002

(54) LOBELIA PLANT NAMED 'LAGUNA BLUE ICE'

(76) Inventor: Reinhard W. Rother, 56 Emerald Monbulk Rd., Emerald, Victoria 3782 (AU)

( * ) Notice: Subject to any disclaimer, the term of this patent is extended or adjusted under 35 U.S.C. 154(b) by 32 days.

(21) Appl. No.: 09/837,580

(22) Filed: Apr. 19, 2001

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A distinct cultivar of Lobelia plant named 'Laguna Blue Ice', characterized by its compact and mounding plant habit; freely branching habit; dense and bushy plant form; uniform and continuous flowering; and blue-colored flowers.

1 Drawing Sheet

BACKGROUND OF THE INVENTION

The present Invention relates to a new and distinct cultivar of Lobelia plant, botanically known as *Lobelia erinus L.*, and hereinafter referred to by the name 'Laguna Blue Ice'.

The new Lobelia is a product of a planned breeding program conducted by the Inventor in Emerald, Victoria, Australia. The new Lobelia originated from a cross made by the Inventor of two unidentified proprietary *Lobelia erinus L.* selections. The new Lobelia was selected by the Inventor in 1998 as a single plant within the progeny of the cross on the basis of its compact plant habit.

Asexual reproduction of the new cultivar by terminal cuttings taken at Emerald, Victoria, Australia, since 1998, has shown that the unique features of this new Lobelia are stable and reproduced true to type in successive generations.

SUMMARY OF THE INVENTION

Plants of the cultivar Laguna Blue Ice have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Laguna Blue Ice'. These characteristics in combination distinguish 'Laguna Blue Ice' as a new and distinct cultivar:

1. Compact and mounding plant habit.
2. Freely branching, dense and bushy plant form.
3. Uniform and continuous flowering.
4. Blue-colored flowers.

Plants of the cultivar Laguna Blue Ice are more compact, flower more uniformly and have lighter blue-colored flowers than plants of the parent selections. Compared to plants of the cultivar Laguna Blue, not patented, plants of the new Lobelia are more compact, more outwardly spreading and flower more uniformly.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lobelia.

The photograph at the top of the sheet comprises a side perspective view of four typical flowering plants of 'Laguna Blue Ice' grown in a 22-cm container for 14 weeks.

The photograph at the bottom of the sheet comprises a close-up view of typical flowers and leaves of 'Laguna Blue Ice'.

DETAILED BOTANICAL DESCRIPTION

The following observations and measurements describe plants grown in Bonsall, Calif., under commercial practice during the summer and autumn in an open field with day temperatures ranging from 18 to 35° C. and night temperatures ranging from 8 to 18° C. Four rooted cuttings were planted in 22-cm containers, pinched twice and grown for about 14 weeks. In the following description, color references are made to The Royal Horticultural Society Colour Chart except where general terms of ordinary dictionary significance are used.

Botanical classification: *Lobelia erinus L.* cultivar Laguna Blue Ice.

Parentage:

*Female parent.*—Unidentified proprietary *Lobelia erinus L.* selection, not patented.

*Male parent.*—Unidentified proprietary *Lobelia erinus L.* selection, not patented.

Propagation:

*Type cutting.*—Terminal vegetative cuttings.

*Time to initiate roots.*—Summer: About 15 to 18 days at 22 to 24° C. Winter: About 18 to 21 days at 22 to 24° C.

*Time to develop roots, summer and winter.*—About 35 days at 22 to 24° C.

*Root description.*—Fine, white.

*Rooting habit.*—Freely branching, dense.

Plant description:

*Form.*—Compact and mounding flowering plants with blue-colored flowers. Lateral shoots outwardly spreading; plants uniform. Freely branching with lateral branches forming at every node; dense and bushy. Appropriate for 12-cm containers and 25-cm hanging basket containers.

*Crop time.*—About 8 to 10 weeks are required to produce finished flowering plants in 12-cm containers.

*Plant height.*—About 22 cm.

*Plant diameter.*—About 27.5 cm.

*Vigor.*—Vigorous growth habit.

*Lateral branch description.*—Length: About 32 cm. Diameter: About 1.75 mm. Internode length: About 1.9 cm. Cross-section: Square. Texture: Smooth. Color: 144B.

*Foliage description.*—Leaves simple, alternate. Aspect: Mostly flat. Length: About 3 cm. Width: About 2.3 cm. Shape: Elliptic to obovate. Apex: Rounded to acute. Base: Attenuate. Margin: Crenate. Texture: Smooth, glabrous. Petiole length: About 1.2 cm. Petiole diameter: About 3 mm. Color: Young foliage, upper surface: 146A. Young foliage, lower surface: 146B. Mature foliage, upper surface: 146A; veins, 144B. Mature foliage, lower surface: 147B; veins, 147B. Petiole: 144A.

Flower description:

*Flower type and habit.*—Single axillary flowers, Flowers initially upright then held outwardly. Freely and continuously flowering, about 8 opening and open flowers per lateral branch. Older flowers are overgrown by new flowers and foliage. Flowers not fragrant. Flowers persistent.

*Flower shape.*—Three larger lower petals and two upright petals, fused at base; zygomorphic.

*Natural flowering season.*—April through November in southern California.

*Flower longevity on the plant.*—Longevity of individual flowers is highly dependent on weather conditions. Typically three to 10 days.

*Flower size.*—Diameter: About 1.7 cm. Depth (height): About 2.2 cm. Tube length: About 1.3 cm. Throat diameter, distal end: About 5 mm. Tube diameter, proximal end: About 3 mm.

*Flower buds.*—Length: About 1.4 cm. Diameter: About 3.5 cm. Shape: Oblong. Color: 97A to 97B.

*Petals.*—Arrangement: Single whorl of five petals, fused at base; three larger lower petals and two smaller upper petals. Three lower petals: Shape: Elliptic. Length, above throat: About 1.2 cm. Width: About 3 mm. Two upper petals: Shape: Narrowly elliptic. Length, above throat: About 6 mm. Width: About 1.5 mm. Upper and lower petals: Apex: Acute to slightly acuminate. Margin: Entire Texture: Smooth, satiny. Color: Petal, upper surface, when opening: 96D to 97A. Petal, lower surface, when opening: 97B. Petal, upper surface, opened flower: 96B. Petal, lower surface, opened flower: 97B to 97C. Throat: White, 155C to 155D, background with dark bluish purple, 95A, nectar guides and two yellow, close to 1B, raised bumps between the nectar guides.

*Sepals.*—Arrangement: Single whorl of five sepals fused at base, star-shaped. Calyx length: About 8 mm. Calyx diameter: About 5 mm. Shape: Narrowly elliptic. Apex: Acute. Margin: Entire. Texture: Smooth, thin. Color, both surfaces: 147B.

*Peduncle.*—Strength: Flexible and wiry. Length: About 2 cm. Diameter: About 1 mm. Aspect: About 45° from stem axis. Color: 144A.

*Reproductive organs.*—Stamens: Quantity: About five; filaments free, anthers fused around stigma. Filament color: 96D to 97D. Anther length: About 2 mm. Anther shape: Oblong. Anther color: 188A. Pollen amount: Scarce. Pollen color: 188A. Pistils: Quantity: One. Pistil length: About 1 cm. Stigma shape: Rounded. Stigma color: 96A. Style length: About 9 mm. Style color: 144C. Ovary color: 144C.

*Seed.*—Seed production has not been observed.

Disease/pest resistance: Plants of the new Lobelia have not been noted to be resistant to pathogens or pests common to Lobelia.

Weather tolerance: Plants of the new Lobelia have exhibited good tolerance to rain and wind.

It is claimed:

1. A new and distinct cultivar of Lobelia plant named 'Laguna Blue Ice', as illustrated and described.

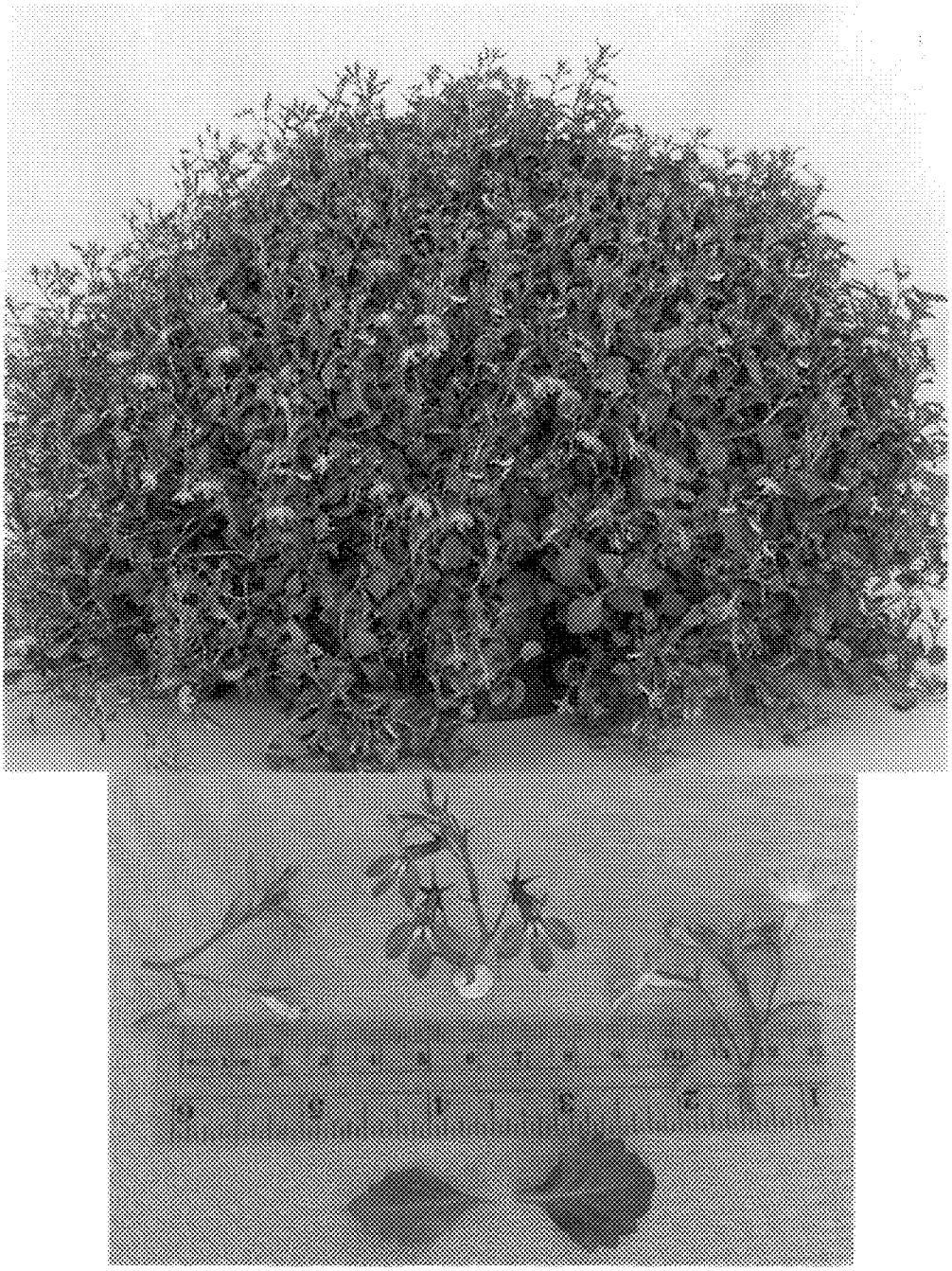

* * * * *